US00PP29692P2

(12) United States Plant Patent
Cho

(10) Patent No.: US PP29,692 P2
(45) Date of Patent: Sep. 18, 2018

(54) ***COLOCASIA* PLANT NAMED 'ALOHA'**

(50) Latin Name: *Colocasia escuelenta*
Varietal Denomination: Aloha

(71) Applicant: John J. Cho, Paia, HI (US)

(72) Inventor: John J. Cho, Paia, HI (US)

( * ) Notice: Subject to any disclaimer, the term of this patent is extended or adjusted under 35 U.S.C. 154(b) by 0 days.

(21) Appl. No.: 15/530,848

(22) Filed: Mar. 8, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

(56) References Cited

PUBLICATIONS planthaven.com/collection/colocasia-royal-hawaiian-series/ Jul. 1, 2015.*

* cited by examiner

*Primary Examiner* — Annette H Para
(74) *Attorney, Agent, or Firm* — Barbara Campbell; Cochran Freund & Young LLC

(57) ABSTRACT

A new variety of *Colocasia* plant named 'Aloha' that is characterized by large glossy sagittate leaves which emerge dark olive-green in color and rapidly become dark purple-black in color. The under surfaces of the leaves of 'Aloha' exhibit prominent raised veining which is contrasting light green in color. 'Aloha' produces numerous closely-attached basal shoots such that mature plants of 'Aloha' are dense in overall habit.

3 Drawing Sheets

Genus and species: *Colocasia escuelenta.*
Variety denomination: 'Aloha'.

BACKGROUND OF THE NEW PLANT

The present invention relates to a new and distinct variety of *Colocasia* commonly known as the taro plant or elephant ears. *Colocasia* is grown as a food crop or for use as an ornamental plant for planting in containers or in the landscape. The new variety is known botanically as *Colocasia esculenta* and will be referred to hereinafter by the variety name 'Aloha'.

*Colocasia* is a tuberous rooted perennial which is native to tropical Asia and Polynesia. It grows to 1.5 m to 2 m in height from starchy tubers. The leaves of *Colocasia* are heart-shaped and very large in size. The tuberous roots are cooked and eaten as a starchy staple in many tropical areas. *Colocasia* are also grown as an ornamental plant for the landscape in warmer climates or as a container plant in colder areas.

The new *Colocasia* variety named 'Aloha' is the product of a long-term breeding program carried out by the inventor in a cultivated area in Kula, Hi. The purpose of the breeding program is to develop new commercial varieties by combining attributes of plant vigor with novel leaf coloration and color combinations, and leaf texture.

'Aloha' arose and was selected by the inventor as a seedling selection from the controlled pollination between the female parent variety *Colocasia* 'Maui Gold' (U.S. Plant Pat. No. 24,482) and male parent variety *Colocasia* 'Coal Miner' (unpatented).

'Aloha' was selected for its large glossy leaves which emerge dark olive-green in color, and whose upper surfaces rapidly become almost entirely purple-black in color, and whose lower surfaces become dark purple-black between the veins and away from the margins. The inventor also observed that 'Aloha' produces numerous closely-attached clumping shoots and petioles such that the whole plant is exceptionally dense in its overall appearance.

The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation". The first asexual propagation of 'Aloha' was carried out by the inventor in Kula, Hi. in 2010 using this method of "huli propagation". Subsequent asexual reproductions by huli propagation and by tissue culture have confirmed to the inventor 'Aloha' is stable, uniform, and reproduces true to type in successive generations of asexual propagation.

SUMMARY

The following traits have been repeatedly observed and represent the distinguishing characteristics of the new *Colocasia* variety named 'Aloha'. 'Aloha' has not been tested under all possible conditions and phenotypic differences may be observed with variations in environmental, climatic and cultural conditions, however, without any variance in genotype:

1. 'Aloha' bears large glossy sagittate leaves.
2. The leaves of 'Aloha' emerge dark olive-green in color.
3. Except for the veins and midrib, the upper surfaces of the leaves of 'Aloha' rapidly become dark purple-black in color, with maturity.
4. The under surfaces of the leaves of 'Aloha' retain their dark olive green color towards the leaf margins and become dark purple-black in color towards and between the midrib and veins.

5. The under surfaces of the leaves of 'Aloha' exhibit prominent raised veining which is light green in color.
6. 'Aloha' produces numerous closely-attached basal shoots such that mature plants of 'Aloha' are dense in overall habit.
7. At maturity, plants of 'Aloha' are between 1.1 meter and 1.25 meters in height, and 0.9 meter to 1.0 meter in width.

DESCRIPTION OF THE PHOTOGRAPHS

The accompanying color photographs illustrate the overall appearance of 'Aloha' showing the colors as true as it is reasonably possible to obtain in colored reproductions of this type. Colors in the photographs may differ from the color values cited in the detailed botanical description, which accurately describe the actual colors of the new variety 'Aloha'.

Photographs were made from plants which were approximately 12-months-old from a tissue culture division and which were grown outdoors. No growth regulators were applied.

DESCRIPTION OF THE NEW VARIETY

Figure 1:
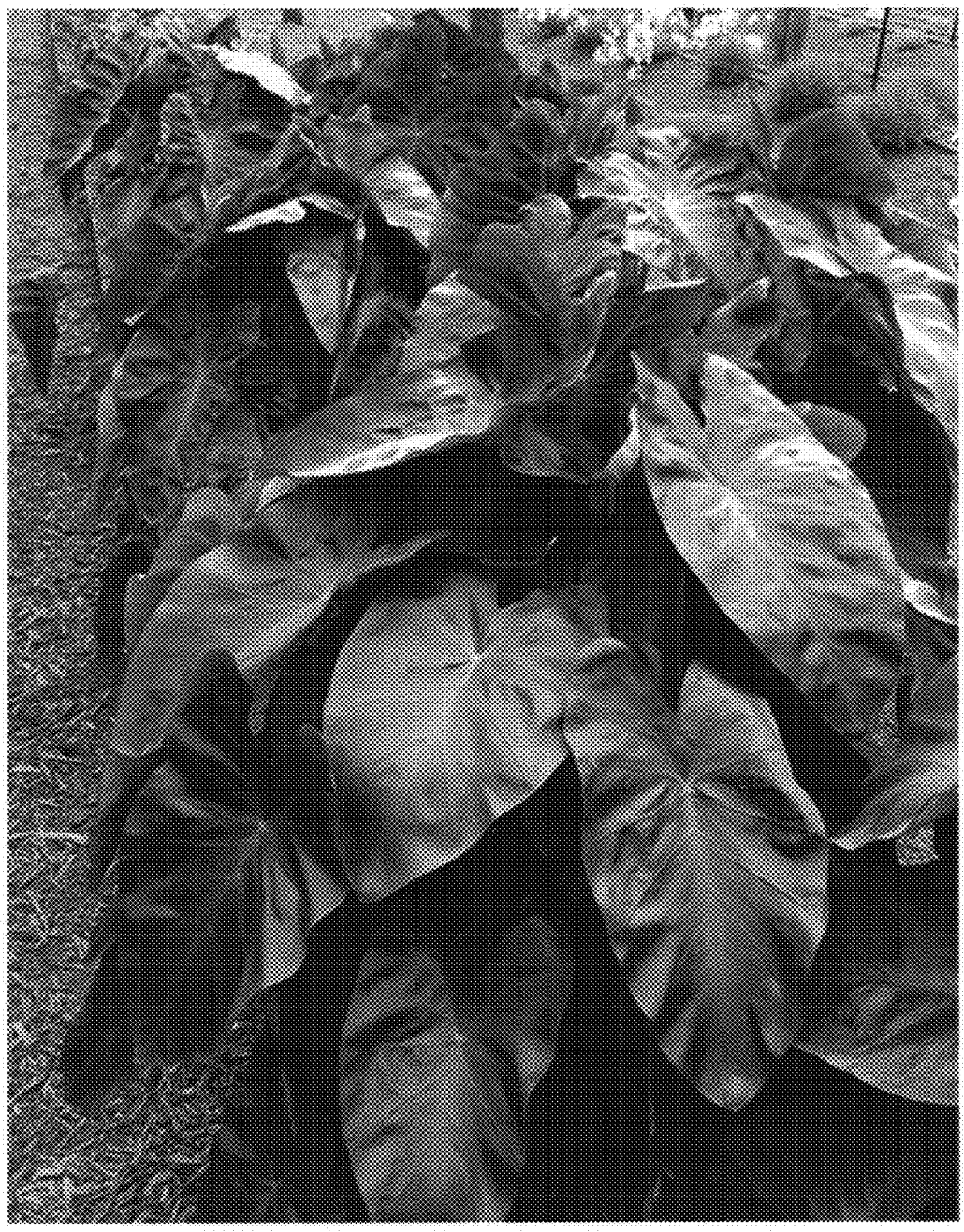
FIG. 1 shows an in-ground planting of 4 plants of 'Aloha'.
Figure 2:
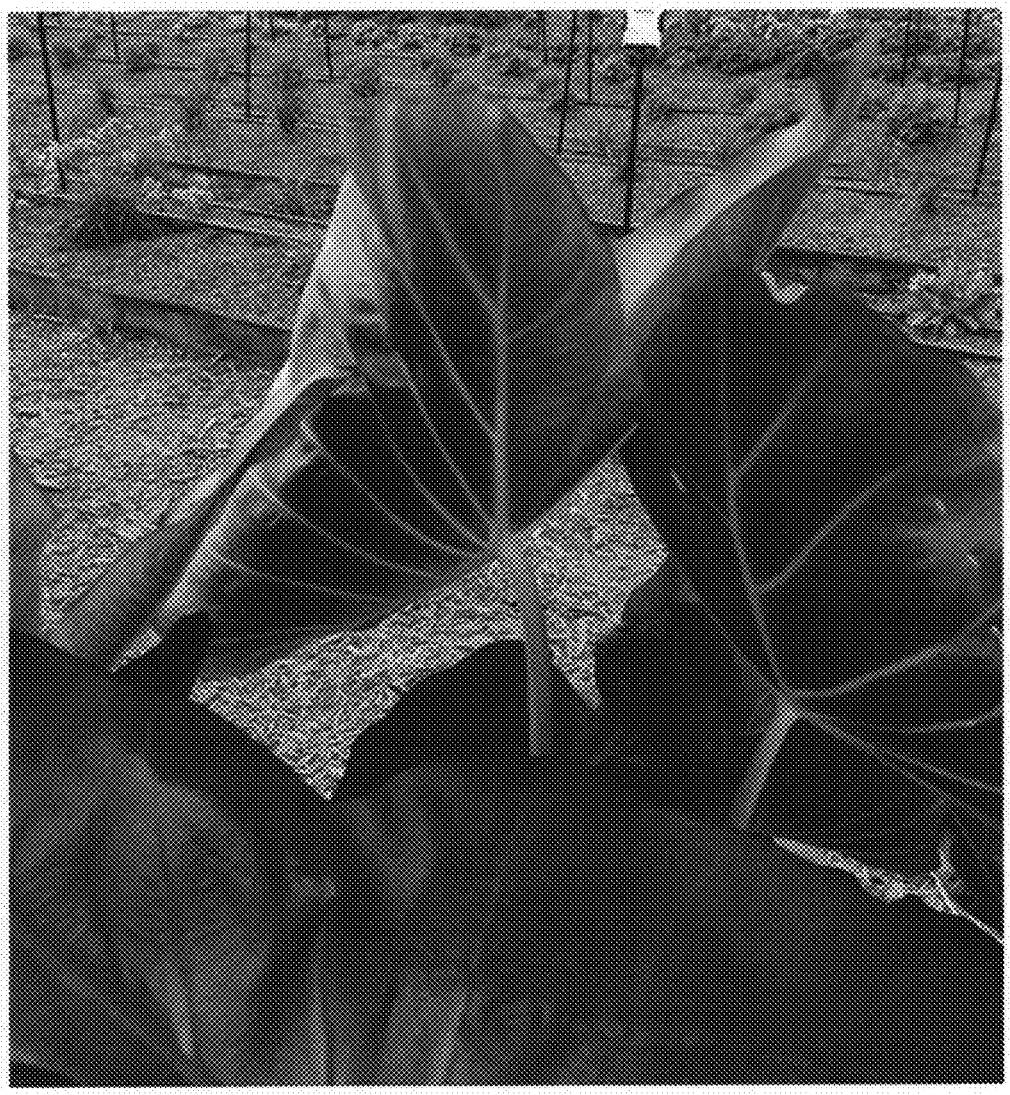
FIG. 2 shows the prominent contrasting light green veins on the underside of the leaves of 'Aloha'.
Figure 3:
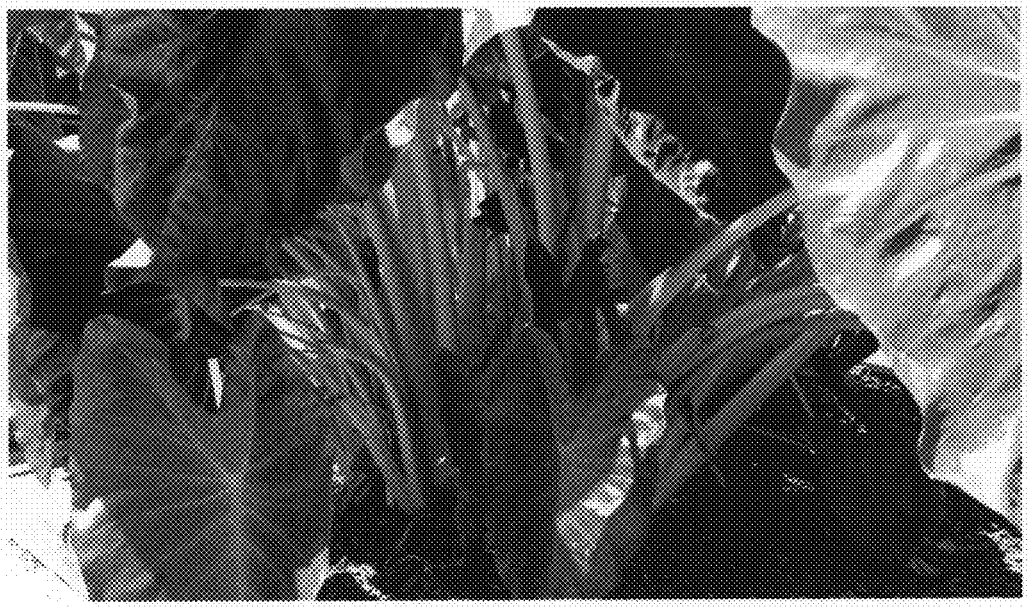
FIG. 3 shows the vigorous basal branching and clumping habit of 'Aloha'.

The following is a detailed description of the new *Colocasia* plant named 'Aloha'. Data were collected from a plant which was 12-months-old from a tissue culture division and grown outdoors in Oxnard, Calif. The color determinations are in accordance with the 2007 edition of The Royal Horticultural Society Colour Chart, London, England, except where general color terms of ordinary dictionary significance are used. The growing requirements are similar to other *Colocasia*.

Botanical classification:

*Genus.*—*Colocasia.*

*Species.*—*esculenta.*

*Denomination.*—'Aloha'.

*Common name.*—Taro or elephant ears.

Plant:

*Plant use.*—Container or landscape plant.

*Cultural requirements.*—Cultural requirements are well draining soil or growing media, full sun to partial shade.

*Tuberous roots.*—System type: Tuberous. Dimensions: 18 cm to 20 cm in length, 8 cm to 10 cm in diameter. Color: 155B.

*Plant vigor.*—Vigorous, prolific basal shoot production.

*Plant growth habit.*—Upright, non-spreading.

*Plant growth rate and crop time.*—A one-gallon container plant grown at 18° C. to 20° C. may be produced in 12 to 16 weeks from a 4 cm cell transplant.

*Plant description.*—A newly-propagated plant of 'Aloha' consists of an excised huli or stem which bears 2-3 petioles and early leaves. As the newly propagated plant is inserted into the soil or growing medium, that plant will produce its own corm, or "mother corm", which in turn will produce new lateral shoots and new basally-attached corms or "cormels". These basal cormels give rise to daughter plants. Daughter plants begin to appear above soil level about 2 to 3 months after planting of the mother plant.

*Plant dimensions.*—110 cm to 125 cm in height and 90 cm to 100 cm in width.

*Plant hardiness.*—USDA Zone 7b.

*Propagation.*—Propagation is accomplished by huli propagation and by tissue culture.

*Time to develop daughter plants.*—Appear above soil around 2 to 3 months after planting.

*Pest or disease susceptibility and resistance.*—'Aloha' has not been found to be more or less susceptible to disease or pests than other cultivars of the genus.

Parentage:

*Female parent.*—*Colocasia* 'Maui Gold' (U.S. Plant Pat. No. 24,482).

*Male parent.*—*Colocasia* 'Coal Miner' (Unpatented).

Foliage:

*Number.*—A one-year old plant of 'Aloha' bears functional 25 to 40 leaves at one time; new leaves appear rapidly, around every 2 to 3 days, due to the profusion of new basal shoots.

*Petioles.*—Length: 75 cm to 90 cm. Width: 8 mm (just below leaf attachment) increasing to 20 mm to 25 mm at the base where attached to corm or cormel. Color: Ranges between N144D and 144C. Sap color: Colorless.

*Leaf.*—Dimensions at maturity: 30 cm to 35 cm in length and 18 cm to 22 cm in width. Average leaf sinus depth: 8 cm to 10 cm. Attitude: Oblique. Aspect: Erect with apex down. Leaf generally slightly folded or cupped. Shape: Sagittate. Margins: Entire, slightly undulating. Apex: Acute. Base: Peltate. Attachment: Petiolate with characteristic tissue formed at junction of leaf blade with the upper termination of the petiole. This area of the leaf tissue is also known as the "piko" and is evident by virtue of its upper surface color being similar to the color of the petiole and contrasting with the leaf color. The principal veins radiate from the piko. Piko color: N144D. Leaf sheath: Open. Texture: Glossy (both surfaces). Leaf color (adaxial surface): Commences 138A as leaf initially unfurls, rapidly becoming dark purple-black ranging between N92A and N186A. Leaf color (abaxial surface): 138A initially and remaining 138A towards margins; elsewhere (constituting approximately half to two-thirds of the abaxial surface), becoming N92A to N186A. Venation: Palmate. Veins: 5 principal veins radiate from the piko: one midrib extending from the piko to the leaf apex, one pair of veins extending laterally towards the widest points of the leaf, and one pair extending towards each of the basal lobe margins. 7 to 8 pairs of secondary veins. Vein color (adaxial surface): Midrib lightest in color, N144C; lateral veins darker, ranging between 147A to N186A. Vein color (abaxial surface): N144A to 144C. Vein prominence (adaxial surface): Slightly depressed. Vein prominence (adaxial surface): Prominently raised, approximately 2 mm in height and 3 mm to 4 mm in width.

Inflorescence, flowers and reproductive organs:

*Inflorescence*.—Arises from the leaf axils. The inflorescence consists of a short peduncle, a spadix, and spathe.

*Peduncle*.—Dimensions: 18 cm to 28 cm in length, 0.4 cm to 0.65 cm in width. Shape (cross-section): Triangular. Color: 145C. Surface: smooth.

*Spadix* (*botanically a spike*).—Arrangement: Fleshy central axis to which small sessile flowers are attached. Dimensions: 9.5 cm to 10 cm in length. Flowers: Female flowers at the base, male flowers towards the tip, and sterile flowers in between. The extreme tip or appendage of the spadix has no flowers at all.

*Spathe*.—Appears as large yellowish bract which sheathes the spadix. Dimensions: 19.5 cm to 21.5 cm in length. Lower section of spathe: Color, light-green, 145C, and wraps tightly around the spadix and completely occludes the female flowers from view. Upper section of spathe: Color, yellow, 13B, and rolled inward at the apex, but remaining open on one side to reveal the male flowers on the spadix. Central section of spathe: Narrow neck, corresponding to the region of the sterile flowers on the spadix.

*Seed*.—Seed is not produced naturally since male and female flowers within each inflorescence do not mature at the same time. Pollination can be achieved manually or in nature, only with the presence of small insect pollinators which are found in regions of genetic origin of the species, and not Hawaii.

COMPARISON TO PARENTAL LINES AND COMMERCIAL VARIETY

When 'Aloha' is compared to the female parent, *Colocasia* 'Maui Gold', 'Maui Gold' bears chartreuse-golden glossy leaves on petioles which range in color from white to light yellow to light burgundy, while the leaves of 'Aloha' are dark olive-green then purple-black in color and borne on uniformly light green petioles. In addition, the area of attachment (known as the piko) of the petioles to the leaves of 'Maui Gold' is burgundy in color, whereas the piko of 'Aloha' is light green in color.

When 'Aloha' is compared to the male parent, *Colocasia* 'Coal Miner', 'Coal Minder' bears similarly dark purple-black leaves, the surfaces of the leaves of 'Coal Miner' are matte in texture, while the leaves of 'Aloha' are glossy. In addition, whereas 'Aloha' produces numerous basal shoots and remains highly clumping in habit, the new shoots of 'Coal Miner' are attached to the mother plant by stolons such that plants of 'Coal Miner' have an open, non-clumping, habit. In addition, the mature height of 'Coal Miner' ranges between 1.5 meters and 1.75 meters, whereas the mature height of 'Aloha' ranges between 1.1 meters and 1.25 meters.

The closest comparison variety in commerce known to the inventor is *Colocasia* 'Coal Miner' which is compared with 'Aloha' above.

I claim:

1. A new and distinct variety of *Colocasia* plant named 'Aloha' as illustrated and described herein.

* * * * *